United States Patent

Lösel et al.

[11] 4,021,547
[45] May 3, 1977

[54] 3β-(α-L-ALTHROMETHYLOSYL)-14β-HYDROXY-BUFA-4,20,22-TRIENOLIDE AND ACYLATED DERIVATIVES THEREOF

[75] Inventors: Walter Lösel, Ingelheim am Rhein; Werner Traunecker, Munster-Sarmsheim; Wolfgang Hoefke, Budenheim, all of Germany

[73] Assignee: Boehringer Ingelheim GmbH, Ingelheim am Rhein, Germany

[22] Filed: Jan. 21, 1976

[21] Appl. No.: 651,045

[30] Foreign Application Priority Data

Feb. 1, 1975 Germany .......................... 250195

[52] U.S. Cl. .................................... 424/182; 536/6
[51] Int. Cl.² ...................................... A61K 31/705
[58] Field of Search ............... 260/210.5; 424/182; 536/6

[56] References Cited

UNITED STATES PATENTS 3,472,836 10/1969 Vogelsang ...................... 260/210.5

Primary Examiner—Lewis Gotts
Assistant Examiner—Cary Owens
Attorney, Agent, or Firm—Hammond & Littell

[57] ABSTRACT

Compounds of the formula

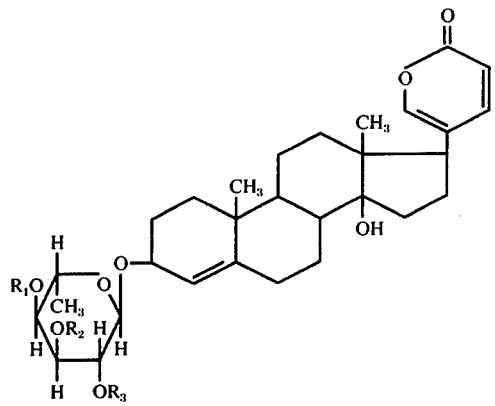

wherein $R_1$, $R_2$ and $R_3$ are hydrogen or carboxylic acyl, particularly acetyl, benzoyl or p-nitro-benzoyl; the compounds are useful as cardiotonics.

6 Claims, No Drawings

3β-(α-L-ALTHROMETHYLOSYL)-14β-HYDROXY-BUFA-4,20,22-TRIENOLIDE AND ACYLATED DERIVATIVES THEREOF

This invention relates to novel 3β-(α-L-altromethylosyl)-14β-hydroxy-bufa-4,20,22-trienolides, as well as to methods of preparing these compounds.

More particularly, the present invention relates to a novel class of pyranosides represented by the formula

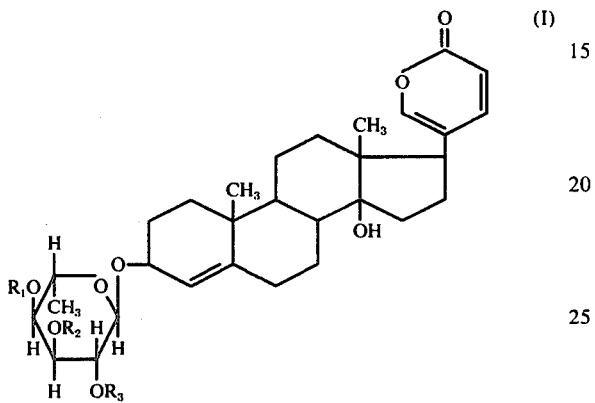

wherein $R_1$, $R_2$ and $R_3$ are hydrogen or carboxylic acyl, such as acetyl, benzoyl or p-nitro-benzoyl.

The compounds embraced by formula I may be prepared by the following methods:

Method A

By reducing a 2′,4′-diacylated proscillaridin of the formula

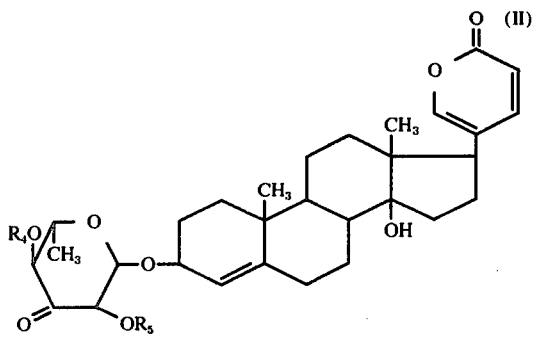

wherein $R_4$ and $R_5$ are carboxylic acylc, especially acetyl, benzoyl or p-nitro-benzoyl, with a complex metal hydride and, if it is desired to obtain a compound of the formula I wherein $R_1$, $R_2$ and $R_3$ are hydrogen, simultaneously or subsequently removing the carboxylic acyl groups by hudrolysis.

For instance, if a 2′,4′-diacyl-3′-oxo-proscillaridin of the formula II is used as the starting material and lithium tri-tert.butoxy aluminum hydride as the reducing agent, the reaction sequence is as follows:

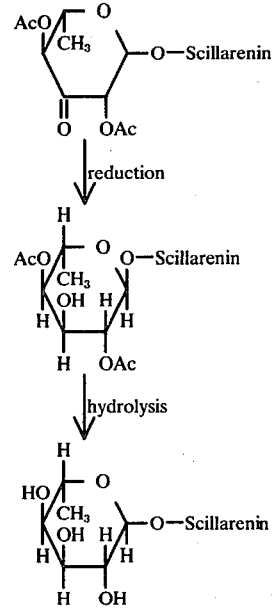

where Ac is carboxylic acyl.

The reduction of the 2′,4′-diacyl-3′-oxo-proscillaridin is carried out in an anhydrous solvent at temperatures between −5° and +30° C.

Examples of suitable complex hydrides besides lithium tri-tert.butoxy aluminum hydride are sodium borohydride, sodium cyano borohydride and other, modified complex hydrides, such as potassium tri-isopropoxy borohydride and lithium or potassium tri-sec.-butyl borohydride. However, the use of lithium tri-tert.butoxy aluminum hydride or sodium borohydride as the reducing agent is preferred.

Examples of suitable anhydrous solvent media are dioxane, tetrahydrofuran, methanol and ethanol. When lithium tri-tert.butoxy aluminum hydride is used as the reducing agent, anhydrous dioxane or anhydrous tetrahydrofuran is preferred as the solvent medium.

When the reduction is carried out with lithium tritert.butoxy aluminum hydride or sodium borohydride as the reducing agent, followed by working up of the reaction mixture and hydrolysis of the acyl groups, the end product is a mixture consisting mainly of a compound of the formula I wherein the pyranosyl moiety is an L-altromethylosyl radical and a very small amount of side-products which can be separated by chromatographic purification.

The optimum reduction reaction time depends largely upon the structure of the starting compound of the formula II and may easily be determined by chromatographic surveillance of the reaction progress. As a rule, the reduction of the 3′-oxo group of the rhamnosyl moiety is complete after a few minutes.

The subsequent hydrolysis for the removal of the acyl groups is carried out in the presence of a water-miscible solvent and of a weak base, such as an aqueous solution of sodium bicarbonate, potassium bicarbonate or ammonia, at a temperature up to the boiling point of the particular solvent which is used, for instance at 100° C.

The starting compounds of the formula II are readily accessible, for example by oxidation of a 2′,4′-diacylproscillaridin with dicyclohexyl-carbodiimide in the presence of a pyridinium salt.

Method B

By reacting the aglycone β-scillarenin with a triacylated 1-halo-pyranose of the formula

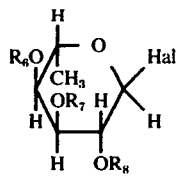

wherein
$R_6$, $R_7$ and $R_8$ are carboxylic acyl, especially acetyl, benzoyl or p-nitro-benzoyl, and
Hal is halogen, especially chlorine, bromine or iodine,
in the presence of a heavy metal salt, and optionally in the presence of a basic catalyst, in an inert solvent while simultaneously removing the water released by the reaction, and subsequently, if desired, hydrolizing the 2',3',4'-triacylated glycoside thus obtained to form the compound of the formula I wherein $R_1$, $R_2$ and $R_3$ are hydrogen.

Examples of suitable heavy metal salts are primarily the carbonates, oxides or cyanides of the heavy transition elements of the Periodic Chart of the Elements (see inside front cover of the Merck Index, 8th Ed.), such as silver, mercury or cadmium, and especially silver carbonate, silver oxide, mercuric oxide, mercuric cyanide or cadmium carbonate; however, zinc chloride or a silver salt of an aliphatic or aromatic α-, β- or γ-hydroxy-carboxylic acid may also be used.

Examples of suitable basic catalysts are the carbonates, bicarbonates, oxides or hydroxides of the base-forming elements of the first to third main groups of the Periodic System of Elements, such as sodium bicarbonate, potassium bicarbonate, calcium carbonate, magnesium oxide, calcium oxide and aluminum hydroxide; however, tertiary aromatic or aliphatic amines, such as pyridine, quinoline, 2,6-lutidine, collidine or triethylamine, may also be used. A tertiary amine may at the same time serve as the solvent medium for the reaction, provided it is present in sufficient excess over the required catalytic amount. In general, 1 to 5 molequivalents of the base, based on the amount of aglycone, are provided.

The reaction of the aglycone with The 1-halo-2,3,4-triacyl-pyranose of the formula III is advantageously carried out in a solvent medium which acts as an entrainment agent and continuously removes the water released by the reaction by azeotropic distillation. Examples of suitable such solvents or solvent mixtures are chloroform, benzene, toluene, 1,2-dichloro-ethane, trichloro-ethane benzene/dioxane, toluene/dichloroethane or the like. Accordingly, the reaction is carried out at the boiling point of the particular solvent medium which is used.

The solvent medium is continuously replaced at the same rate at which it is distilled off. Alternatively, the reaction may be performed in a vessel equipped with a reflux cooler and passing the refluxing solvent through an extractor charged with a drying agent which removes the water from the returning solvent. Examples of suitable drying agents are hydroxides, oxides or sulfates of alkali metals, alkaline earth metals or earth metals. The drying agent may, however, also be added to the reaction mixture, in which case the reaction is advantageously carried out while vigorously stirring the reaction mixture. Of cOurse, the solvent medium may also be allowed to evaporate slowly during the reaction without replacing it.

The reaction is most advantageously performed by dissolving or suspending the aglycone in the solvent medium, heating the solution or suspension to its boiling point, and adding the triacylated 1-halo-pyranose and the heavy metal salt in portions at regular intervals. Another advantageous procedure is to initially provide the aglycone and The triacylated 1-halo-pyranose, together with a portion of the total required amount of the heavy metal salt and the catalytic amount (about 0.1 to 3%, based on the amount of pyranose) of the basic catalyst, allow this reaction mixture to react for anywhere from 5 minutes to 10 hours, depending upon the boiling point of the solvent medium and the reaction rate of the reactants, and add the remainder of the pyranose and the heavy metal salt in 3 to 5 portions at regular intervals. Altogether, an about 1- to 3-fold excess of triacylated b 1-halo-pyranose and heavy metal salt is used.

Sometimes, it is advantageous to carry out the reaction in an atmosphere of an inert gas, such as nitrogen or argon, for example.

The subsequent hydrolysis of the carboxylic acyl groups is performed in a manner which is conventional in sugar chemistry or for the hydrolysis of acylated cardiac glycosides, such as with sodium bicarbonate or potassium bicarbonate in an aqueous ethanolic medium or with ammonia in methanol or ethanol.

The 1-halo-2,3,4-triacyl-pyranoses of the formula III may themselves by obtained from the corresponding tetraacyl-L-pyranoses by reaction with hydrochloric, hydrobromic or hydroiodic acid in glacial acetic acid.

The following examples illustrate the present invention and will enable others skilled in the art to understand it more completely. It should be understood, however, that the invention is not limited solely to the particular examples given below.

EXAMPLE 1

3β-(α-L-Altromethylosyl)-14β-hydroxy-bufa-4,20,22-trienolide by method A 4.35 gm (18 millimols) of lithium tri-tert.butoxy aluminum hydride were added to a solution of 3.6 gm (6 millimols) of 3β-(2',4'-diacetyl-3'-oxo-α-L-rhamnosyl)-14β-hydroxy-bufa-4,20,22-trienolide in 100 ml of absolute dioxane at 0° C, and the mixture was stirred for 10 minutes on an ice bath. Thereafter, the excess complex hydride reducing agent was destroyed by adding 2 N acetic acid, the acidic solution was diluted with ethyl acetate, and the resulting solution was thoroughly washed first with an aqueous 5% sodium bicarbonate solution and then with water. The organic solution was now dried over sodium sulfate, and the solvent was then evaporated in vacuo.

The residue, 3β-(2',4'-diacetyl-α-L-rhamnosyl)-14β-hydroxy-bufa-4,20,22-trienolide, ws taken up in 100 ml of methanol, the resulting solution was heated to 60° C, 10 ml of a half-saturated aqueous sodium bicarbonate solution were added, and the mixture was stirred for about 1 hour until the hydrolysis had gone to completion (thin-layer chromatogram comparison). The reaction mixture was then evaporated to a small volume in vacuo, diluted with ethyl acetate, extracted twice with 30 ml of 2 N hydrochloric acid each, and washed with water until free of acid. The organic phase was dried over sodium sulfate and evaporated in vacuo, and the residue was purfied on a silicagel column (0.2–0.5 mm grain size) in the system chloroform-methanol (100 + 4) and then crystallized from ethyl acetate, yielding 2.84 gm (89% of theory) of the compound of the formula

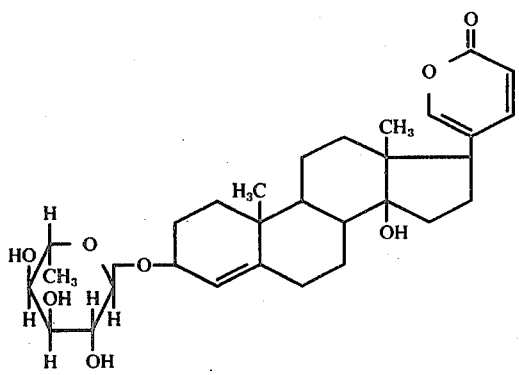

which had a melting point of 196° –201° C.

EXAMPLE 2

Using a procedure analogous to that described in Example 1, 3β-[2'-(β-phenyl-propionyl)-4'-acetyl-α-L-rhamnosyl]-14β-hydroxy-bufa-4,20,22-trienolide and 3.42 gm (92% of theory) of 3β-(α-L-altromethylosyl)-14β-hydroxy-buffa-4,20,22-trienolide, m.p. 196–202° C, were obtained by reducing 4.84 gm (7 millimols) of 3β-[2'-(β-phenyl-propionyl)-4'-acetyl-3'-oxo-α-L-rhamnosyl]-14β-hydroxy-bufa-4,20,22-trienolide with 0.16 gm (4 millimols) of sodium borohydride in 100 ml of absolute dioxane.

EXAMPLE 3

Using a procedure analogous to that described in Example 1, 3β-[2',4'-dibenzoyl-α-L-rhamnosyl]-14β-hydroxybufa-4,20,22-trienolide and 1.48 gm (88% of theory) of 3β-(α-L-altromethylosyl)-14β-hydroxy-bufa-4,20,22-trienolide, m.p. 196° –201° C, were obtained by reducing 2.18 gm (3 millimols) of 3β-[2',4'-dibenzoyl-3'-oxo-α-L-rhamnosyl]-14β-hydroxy-bufa-4,20,22-trienolide with 0.17 gm (4 millimols) of sodium borohydride in 50 ml of absolute methanol.

EXAMPLE 4

3β-(2',3',4'-Triacetyl-α-L-altromethylosyl)-14β-hydroxy-buta-4,20,22-trienolide by method B A solution of 3.5 gm (10 millimols) of 1-bromo-2,3,4-triacetyl-L-altromethylose in 10 ml of ethylene chloride and 1.30 gm (5 millimols) of mercuric cyanide were added to a solution of 0.960 gm (2.5 millimols ) of β-scillarenin in 20 ml of ethylene chloride, and the resulting mixture was boiled for 3 hours in an atmosphere of nitrogen. Thereafter, the ethylene chloride was slowly distilled off, the residue was stirred with ethyl acetate, the mixture was filtered, and the filtrate was evaporated. The residue was chromatographed on a silicagel column (0.2 to 0.5 grain size) in the system chlorogorm : acetone : ethyl acetate (80:15:10), the fractions containing the desired compound were combined and evaporated, and the residue was crystallized from ethyl acetate/petroleum ether (b.p. 40°–80° C), yielding 0.481 gm (29% of theory) of the compound of the formula

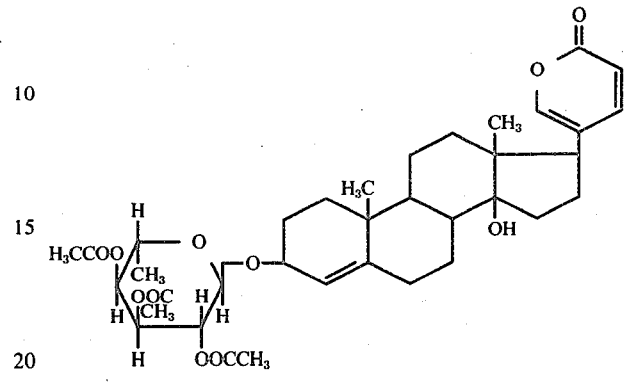

which had a melting point of 240° –243° C.

The compounds embraced by formula I above have useful pharmacodynamic properties. More particularly, they exhibit positive inotropic activity in warm-blooded animals, such as dogs and guinea pigs, and are therefore useful as cardiotonics for the treatment of cardiac insufficiencies.

The compounds of the present invention combine to a surprising extent all of the desirable property criteria which are expected of a therapeutically useful cardiac glycoside with respect to effectiveness and safety. Thus, the compounds embraced by formula I above are completely absorbed and have an elimination rate within an optimum range, which completely eliminates the danger of cumulative effects, but on the other hand makes it possible to maintain an optimum blood concentration level over short or long periods of time, as required.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmceutical carrier and one effective dosage unit of the active ingredient, such as tablets, coated pills, capsules, wafers, powders, solutions, suspensions, emulsions, syrups, suppositories and the like. One effective cardiotonic dosage unit of the compounds according to the present invention is from 0.00083 to 0.084 mgm/kg body weight, preferably from 0.002 to 0.034 mgm/kg body weight.

The following examples illustrate a few pharmaceutical dosage unit compositions comprising a compound of the present invention as an active ingredient and represent the besT modes contemplated of putting the invention into practical use. The parts are parts by weight unless otherwise specified.

EXAMPLE 5

Tablets
The tablet composition is compounded from the

| | | |
|---|---:|---|
| 3β-(α-L-Altromethylosyl)-14β-hydroxy-bufa-4,20,22-trienolide | 0.25 | parts |
| Lactose | 85.75 | " |
| Potato starch | 30.0 | " |
| Gelatin | 3.0 | " |

-continued

| | | |
|---|---:|---|
| Magnesium stearate | 1.0 | '' |
| Total | 120.0 | parts |

Preparation:

The glycoside is intensively milled with ten times its weight of lactose, the milled mixture is admixed with the remaining amount of the lactose and the potato starch, the resulting mixutre is moistened with an aqueous 10% solution of the gelatin, the moist mass is forced through a 1.5 mm-mesh screen, and the resulting granulate is dried at 40° C. The dry granulate is again passed through a 1 mm/mesh screen, admixed with the magnesium stearate, and the composition is compressed into 120 mgm-tablets in a conventional tablet making machine. Each tablet contains 0.25 mgm of the glycoside and is an oral dosage unit composition with effective cardiotonic action.

EXAMPLE 6

Coated Pills

The pill core composition is compounded from the following ingredients:

| | | |
|---|---:|---|
| $3\beta$-($\alpha$-L-Altromethylosyl)-$14\beta$-hydroxy-bufa-4,20,22-trienolide | 0.25 | parts |
| Lactose | 32.25 | '' |
| Corn starch | 15.00 | '' |
| Polyvinylpyrrolidone | 2.00 | '' |
| Magnesium stearate | 0.50 | '' |
| Total | 50.00 | parts |

Preparation:

The glycoside is intensively milled with 10 times its weight of lactose, the milled mixture is admixed with the remainder of the lactose and the corn starch, the mixture is moistened with an aqueous 15% solution of the polyvinylpyrrolidone, the moist mass is forced through a 1 mmmesh screen, and the resulting granulate is dried at 40° C and again passed through the screen. The dry granulate is admixed with the magnesium stearate, and the resulting composition is compressed into 50 mgm-pill cores which are subsequently coated in conventional manner with a thin shell consisting essentially of a mixture of sugar and talcum and finally polished with beeswax. Each coated pill contains 0.25 mgm of the glycoside and is an oral dosage unit composition with effective cardiotonic action.

EXAMPLE 7

Drop Solution

The solution is compounded from the following ingredients:

| | | |
|---|---:|---|
| $3\beta$-($\alpha$-L-Altromethylosyl)-$14\beta$-hydroxy-bufa-4,20,22-trienolide | 0.0125 | parts |
| Saccharin sodium | 0.3 | '' |
| Sorbic acid | 0.1 | '' |
| Ethanol | 30.0 | '' |
| Flavoring | 1.0 | '' |
| Distilled water q.s.ad | 100.0 | '' |

Preparation:

The glycoside and the flavoring are dissolved in the ethanol, and the sorbic acid and the saccharin sodium are dissolved in the distilled water. The two solutions are uniformly admixed with each other, and the mixed solution is filtered until free from suspended matter. 1 ml of the filtrate contains 0.125 mgm of the glycoside and is an oral dosage unit composition with effective cardiotonic action.

EXAMPLE 8

Hypodermic Solution

The solution is compounded from the following ingredients:

| | | |
|---|---:|---|
| $3\beta$-($\alpha$-L-Altromethylosyl)-$14\beta$-hydroxy-bufa-4,20,22-trienolide | 0.25 | parts |
| Polyethyleneglycol 600 | 700.0 | '' |
| Tartaric acid | 150.0 | '' |
| Distilled water q.s.ad | 3000.0 | '' |
| | | by vol. |

Preparation:

The tartaric acid, the polyethyleneglycol and the glycoside are successively dissolved in a sufficient amount of distilled water to the indicated volume and then filtered until free from suspended matter. The filtrate is filled into white 3 ml-ampules in an atmosphere of nitrogen, which are then sterilized for 20 minutes at 120° C and sealed. Each ampule contains 0.25 mgm of the glycoside, and the contents thereof are an injectable dosage unit composition with effective cardiotonic action.

EXAMPLE 9

Suppositories

The suppository composition is compounded from the following ingredients:

| | | |
|---|---:|---|
| $3\beta$-($\alpha$-L-Altromethylosyl)-$14\beta$-hydroxy-bufa-4,20,22-trienolide | 0.25 | parts |
| Lactose | 4.75 | '' |
| Suppository base (e.g. cocoa butter) | 1695.0 | '' |
| Total | 1700.0 | parts |

Preparation:

The glycoside and the lactose are admixed and the mixture is milled. The milled mixture is uniformly stirred with the aid of an immersion homogenizer into the suppository base, which had previously been melted and cooled to 40° C. The resulting composition is cooled to 37° C, and 1700 mgmportions thereof are poured into cooled suppository molds and allowed to harden therein. Each suppository contains 0.25 mgm of the glycoside and is a rectal dosage unit composition with effective cardiotonic action.

Analogous resluts are obtained when any one of the other compounds embraced by formula I is substituted for the particular glycoside in Examples 5 through 9. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent ot others skilled in the art that the invention is not limited to these particular embodiments, and the various changes and modifications may be made without departing from the spirit of the invention or the scope of the appended claims.

We claim:
1. A compound of the formula

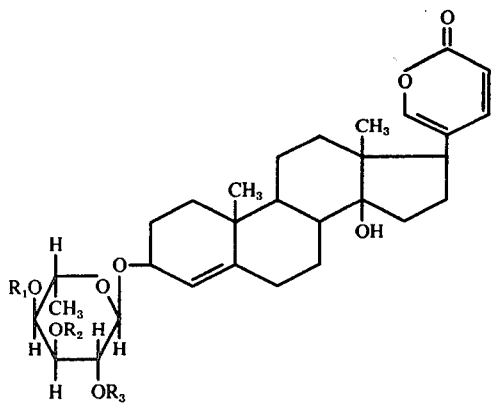

wherein $R_1$, $R_2$ and $R_3$ are each hydrogen, acetyl, benzoyl or p-nitro-benzoyl.

2. A compound of claim 1, where $R_1$, $R_2$ and $R_3$ are each hydrogen, acetyl or benzoyl.

3. The compound of claim 1 which is 3β-(α-L-altromethylosyl)-14β-hydroxy-bufa-4,20,22-trienolide.

4. The compound of claim 1 which is 3β-(2',3',4'-triacetyl-β-L-altromethylosyl)-14β-hydroxy-bufa-4,20,22-trienolide.

5. A cardiotonic pharmaceutical dosage unit composition consisting essentially of an inert pharmaceutical carrier and an effective cardiotonic amount of a compound of claim 1.

6. The method of relieving cardiac insufficiencies in a warm-blooded animal in need of such treatment, which comprises perorally, parenterally or rectally administering to said animal an effective cardiotonic amount of a compound of claim 1.

* * * * *

UNITED STATES PATENT OFFICE
CERTIFICATE OF CORRECTION

Patent No. 4,021,547                Dated May 3, 1977

Inventor(s) WALTER LÖSEL, WERNER TRAUNECKER and WOLFGANG HOEFKE

It is certified that error appears in the above-identified patent and that said Letters Patent are hereby corrected as shown below:

Column 1, line 63, - "hudrolysis" should read -- hydrolysis --.

" 5, " 56, - "buta" should read -- bufa --.

" 5, " 68, - "chlorogorm" should read -- chloroform --.

" 6, " 64, - Should have added -- following ingredients

" 10, " 8, - "B-L" should read -- α-L --.

Signed and Sealed this

Twenty-fifth Day of October 1977

[SEAL]

Attest:

RUTH C. MASON
*Attesting Officer*

LUTRELLE F. PARKER
*Acting Commissioner of Patents and Trademarks*